(12) United States Patent
Seibert

(10) Patent No.: US 6,324,416 B1
(45) Date of Patent: Nov. 27, 2001

(54) CONNECTING DEVICE FOR INTRA-ATRIAL ECG-LEAD

(75) Inventor: Richard L. Seibert, Allentown, PA (US)

(73) Assignee: B. Braun Melsungen AG, Melsungen (DE)

(*) Notice: Subject to any disclaimer, the term of this patent is extended or adjusted under 35 U.S.C. 154(b) by 0 days.

(21) Appl. No.: 09/401,968

(22) Filed: Sep. 23, 1999

(30) Foreign Application Priority Data

Sep. 23, 1998 (DE) .......................................... 298 17 053 U

(51) Int. Cl.[7] .......................................................... A61B 5/04
(52) U.S. Cl. .......................... 600/386; 600/509; 600/523; 439/909; 128/897
(58) Field of Search .............................. 607/115; 439/909, 439/252, 322, 219, 682, 822, 225, 352, 858, 222; 600/394, 386, 509, 523; 128/897

(56) References Cited

U.S. PATENT DOCUMENTS

| 3,445,794 | * | 5/1969 | O'Keefe et al. ...................... 439/848 |
| 3,892,456 | * | 7/1975 | Westmoreland ...................... 439/137 |
| 5,243,995 | | 9/1993 | Maier . | |
| 5,316,494 | * | 5/1994 | Flanagan et al. ...................... 439/352 |
| 5,350,318 | * | 9/1994 | Nees ...................... 439/593 |
| 5,509,822 | * | 4/1996 | Negus et al. ...................... 439/502 |
| 5,769,786 | | 6/1998 | Wiegel . | |

FOREIGN PATENT DOCUMENTS

| 4318963 | 6/1993 | (DE) . |
| 4319033 | 6/1993 | (DE) . |
| 0596344 | 10/1998 | (EP) . |

* cited by examiner

Primary Examiner—Kennedy Schaetzle
Assistant Examiner—Kristen Droesch
(74) Attorney, Agent, or Firm—Diller, Ramik & Wight

(57) ABSTRACT

The connecting device comprises a patient cable with which ECG clamps may be connected to adhesive ECG electrodes to perform an extracorporeal ECG lead. For an intra-atrial ECG lead, an adapter with an ECG clamp is provided, to which adapter an ECG clamp of the patient cable may be connected. The adapter comprises a second input to which a connecting cable may be connected. The associated connector of the connecting cable is designed such that it may selectively be connected directly with an ECG clamp without the adapter being provided.

8 Claims, 3 Drawing Sheets

CONNECTING DEVICE FOR INTRA-ATRIAL ECG-LEAD

BACKGROUND OF THE INVENTION

The present invention refers to a connecting device for intra-atrial ECG-lead and in particular to a connecting device with which the patient cable of an ECG display may be connected to the electric conductor of a vena cava catheter.

A connecting device disclosed in EP 0 596 344 B1 comprises a connecting cable for direct connection with the electric conductor of a vena cava catheter for contacting the atrium, and an adapter to which a connector of the patent cable may be applied and which may be connected with an ECG clamp of the patient cable that is part of a display. Using the patient cable exclusively, an extracorporeal ECG lead may be performed by plugging the three ECG clamps of the patient cable onto ECG electrodes fastened on the patient's body. When the adapter is used in addition, it is possible to perform an intra-atrial ECG lead instead of or in addition to the extracorporeal ECG lead, where an electric conductor extending in a vena cava catheter is advanced into the atrium of the patient. The extracorporeal end of the electric conductor is connected to a second input of the adapter through the connecting cable. It is possible to connect either the first or the second input of the adapter through to the output of the adapter and to transfer the respective potential through the connected ECG clamp of the patient cable to the display. The presence of the adapter is imperative to performing an intra-atrial ECG lead. Without the adapter, the connecting cable is useless, since only an extracorporeal ECG can be recorded using the patient cable.

U.S. Pat. No. 5,243,995 and DE 43 19 033 C1 describe catheter guide wires adapted to be advanced up to the heart, with their tip projecting from a vena cava catheter. Further, DE 43 18 963 C1 describes a device for performing an ECG lead, where the ECG signals are transmitted using an electrolytic liquid forming an electrically conductive liquid column.

U.S. Pat. No. 5,769,786 describes a catheter set offering the possibility of performing an ECG lead, where the ECG signals are transmitted out from the body via a guide wire. To the side of the guide wire, a clamp connected with a connecting wire is applied.

It is an object of the present invention to provide a connecting device comprising a connecting cable and an adapter, which can selectively be used with or without the adapter for an intra-atrial ECG lead.

SUMMARY OF THE INVENTION

According to the invention, the second connector of the present connecting device is a dual connector providing for two possible connections. This connector includes a socket portion matching the plug portion of the adapter, and it further includes a conductive shaft portion to which the ECG clamp may be clamped fittingly. It is an essential advantage that the second connector may selectively be connected with the adapter or with an ECG clamp of the patient cable. It is assumed that the ECG clamp of the adapter is designed substantially like the ECG clamps of the patient cable or that it at least has the same clamping width. Therefore, either the ECG clamp of the patient cable or that of the adapter may engage the shaft portion of the second connector of the connecting cable.

The patient cable thus offers different possibilities for transmitting intra-atrially lead ECG signals to the patient cable. Naturally, the main possibility is to fasten the socket portion of the connector to the plug portion of the adapter. On the other hand, it is also possible to connect the patient cable directly with the second connector of the connecting cable.

The invention further refers to a connecting device for an intra-atrial ECG lead, comprising a conventional patient cable with a plurality of ECG clamps and the present connecting cable. In this case, no adapter is present, yet it may be used optionally.

DESCRIPTION OF THE DRAWINGS

The following is a detailed description of embodiments of the present invention with reference to the accompanying drawings.

In the Figures.

DETAILED DESCRIPTION OF PREFERRED EMBODIMENTS

Figure 1:
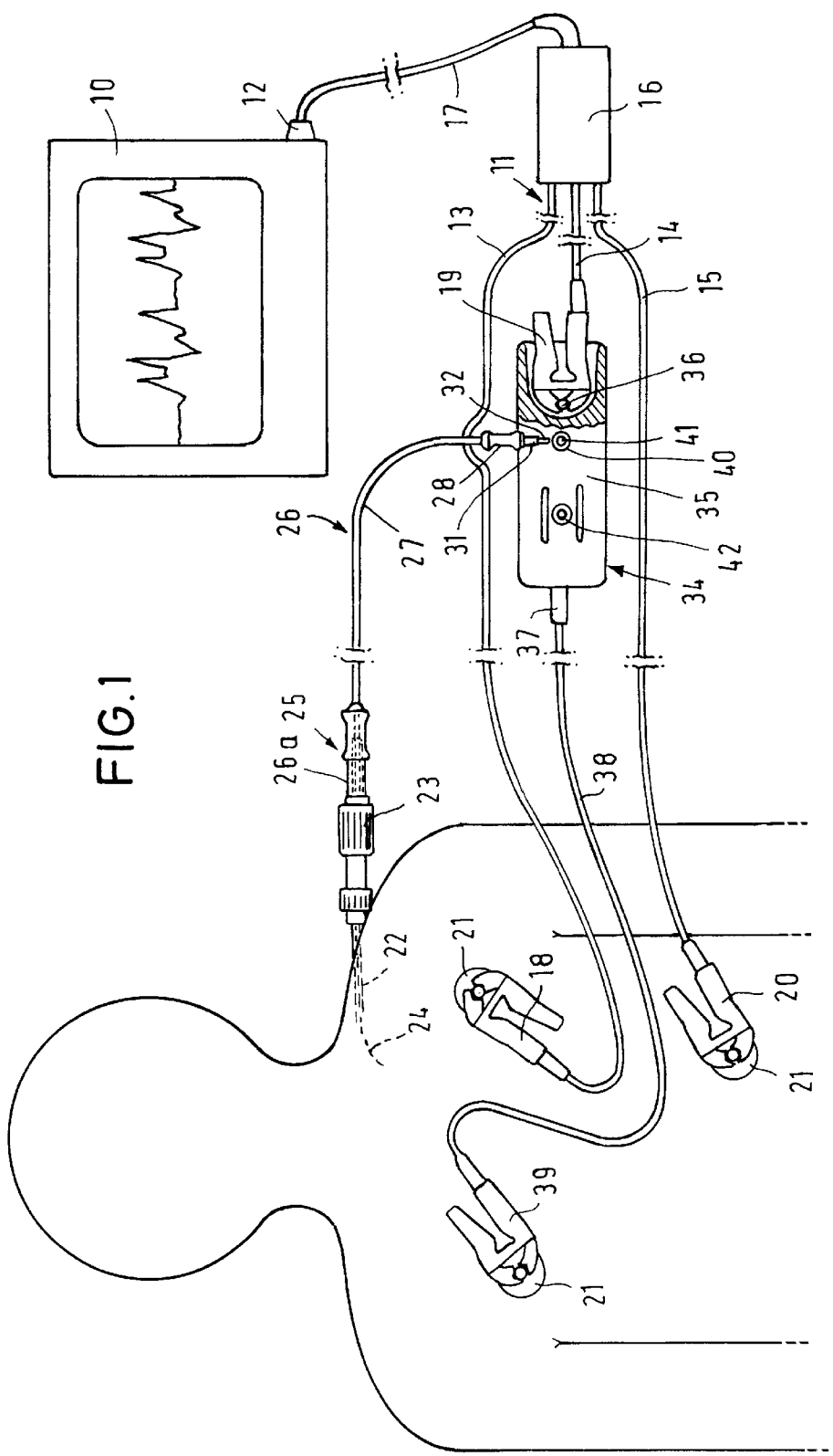
FIG. 1 illustrates different possibilities for an ECG lead via a patient cable using an adapter with and without connecting cable.

FIG. 1 illustrates an ECG display 10 with which ECG voltages may be visualized or recorded, respectively. A patient cable 11 is connected to an input of the ECG display 10 via a multiple plug 12. In the present embodiment, the patient cable 11 has three conductors 13, 14, 15 connected with a distributor 16 from which a multiwire conductor 17 extends to the multiple plug 12. Each of the conductors 13, 14, 15 has an ECG clamp 18, 19, 20 at its end, designed in the manner of a pair of tongs with two clamp legs resiliently pressed against each other. Usually, each ECG clamp 18, 19, 20 is clamped to an ECG electrode 21 fastened to the body of a patient.

A vena cava catheter 22 for the intra-atrial ECG lead is provided with a connecting member 23. Extending through the vena cava catheter 22 is a guide wire 24 to which the connecting member 23 is fixed. The connecting member 23 is generally designed as described in EP 0 486 979 B1. The connecting member 23 comprises an electric conductor connected with the guide wire 24 and having a pin onto which a metal bushing of a connector 25 may be slipped. This bushing is enclosed by an insulating sleeve 26a that simultaneously acts as a protection against accidental contact.

Figure 2:
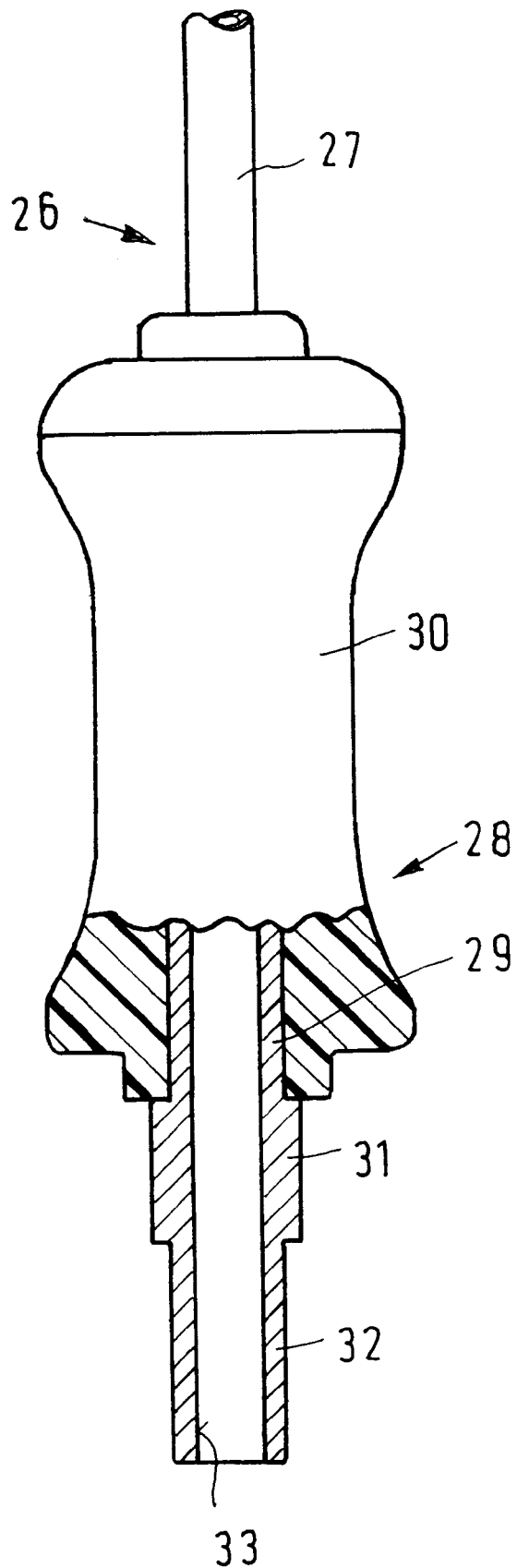
FIG. 2 is a side elevational view of the second connector of the connecting cable in partial section.

The connector 25 is part of a connecting cable 26 comprising an insulated single wire conductor 27. At the other end of the connecting cable 26, there is a second connector 28 illustrated in FIG. 2. The second connector 28 comprises an elongated electrically conductive sleeve 29 extending into a grip portion 30 of plastic material, where it is connected with the wire of the conductor 27. Immediately adjacent the grip portion 30, the sleeve 29 has a shaft portion 31 with an increased outer diameter. A socket portion 32 of reduced outer diameter adjoins the shaft portion 31 coaxially. The outer diameter of the shaft portion 31 is 3.4 mm and that of the socket portion is 2.5 mm. A bore 33 with a diameter of 1.5 mm extends through the sleeve 29. The length of the socket portion 32 is slightly larger than that of the shaft portion 31.

As illustrated in FIG. 1, an adapter 34 is provided to which the ECG clamp 19 of the patient cable 11, connected to the conductor 14, may be connected. The adapter 34 comprises a housing 35 of plastic material provided with an electric output 36 in the form of a pin to which the ECG clamp 19 may be applied. The adapter may further have a plurality of outputs for different types of ECG clamps and thus form a universal adapter as known from EP 0 596 344 B1.

The adapter 34 is provided with a first input 37 to which an ECG clamp 39 is connected via a cable 38. This ECG clamp 39 is also intended to be set onto an ECG electrode 21. The adapter 34 further comprises a second input 40 realized as a pin-like plug portion 41 arranged behind an opening of the housing. Using a switch 42, one may selectively connect either the first input 37 or the second input 40 through to the output 36. Alternatively, it is possible to permanently connect either the first ad/or the second input to the output 36.

The socket portion 32 of the connector 28 may be plugged onto the plug portion 41 of the adapter and be electrically connected with the same. To do this, the socket portion is passed through the housing opening of the adapter. Preferably, the housing opening is large enough to also allow the shaft portion 31 to pass so that the grip portion 30 of insulating material sits immediately on the housing 35.

In practical use of the connecting device, the ECG electrodes 21 are fastened to a patient's body. Afterwards, the ECG clamps 18 and 20 of the patient cable 11 are connected to the respective adhesive electrodes. The ECG clamp 19 of the patient cable intended for a precordial ECG is set into the appropriate socket of the adapter 34, and instead of this ECG clamp, the ECG clamp 39 is connected with the ECG electrode 21 for the precordial ECG. Finally, the connecting cable 26 is connected with both the connecting member 23 and the adapter 34. By actuating the switch 42, it may be selected whether the input 37 or the input 40 is connected through to the output 36 to the display 10. The conductors 13, 15 are permanently connected with the ECG display 10 through the distributor 16.

When the connecting cable 26 is to be used without the adapter 34, the ECG clamp 19 of the patient cable is connected to the second connector 28. This is accomplished by applying the tongs-like legs of the ECG clamp 19 to the shaft portion 31 which they clamp. The outer diameter of the shaft portion 31 is sufficiently large to be retained by the ECG clamp 19.

Figure 3:
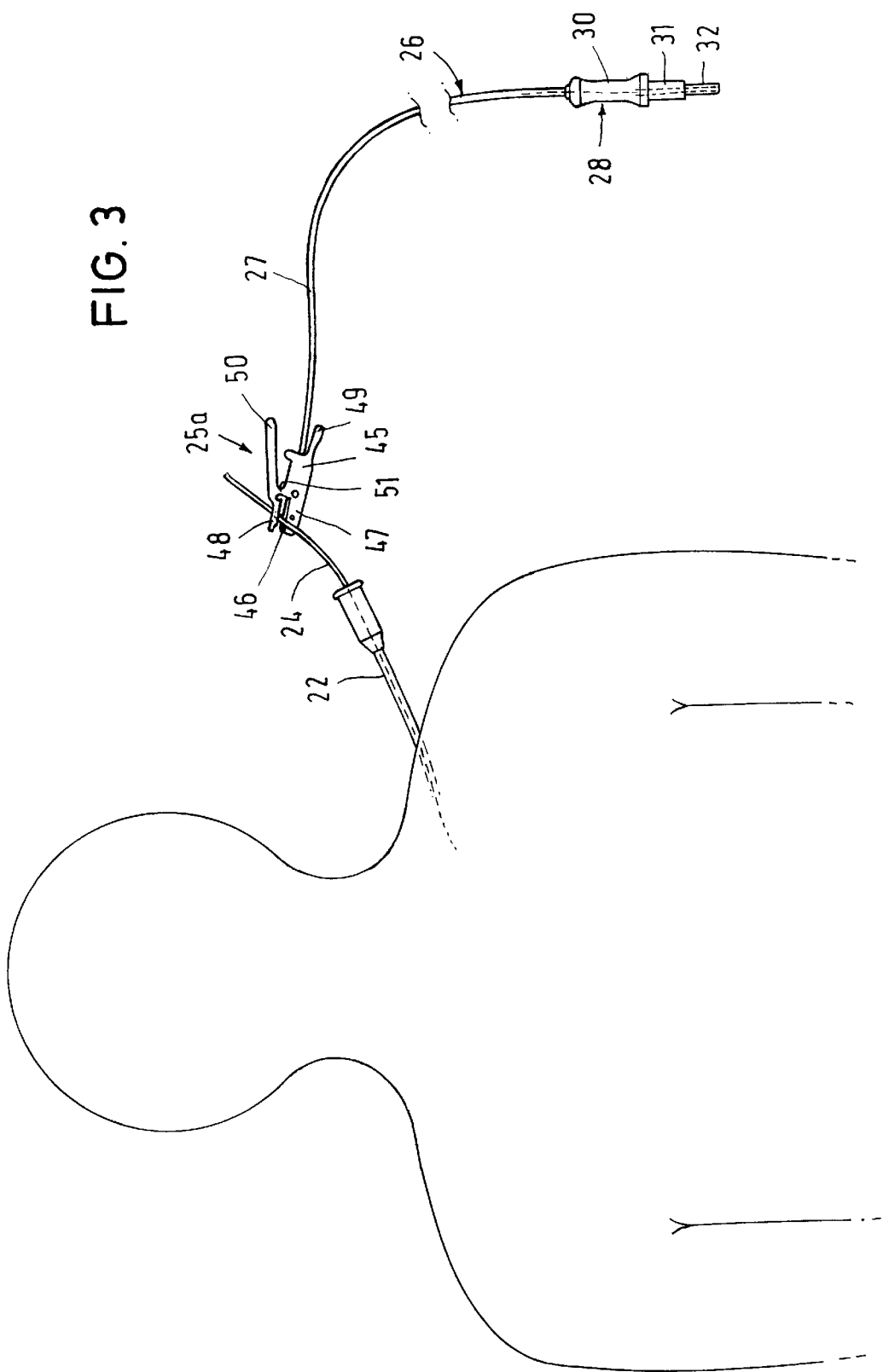
FIG. 3 shows another embodiment of the connecting cable with a clamp adapted to be set onto a catheter guide wire from the side.

FIG. 3 illustrates another embodiment of the connecting cable 26. The second connector 28 is designed in the same way as in the first embodiment, but the first connector 25a differs from the connector 25. The connector 25a is a clamp plugged laterally onto the section of the guide wire projecting from the vena cava catheter 22 and detects the electric ECG signals from this guide wire 24. The clamp 45 comprises a metal plate 46 supported by a supporting leg 47. A pressing leg 48 presses the guide wire 24 against the metal plate 46 connected with the core of the conductor 27. In this manner, the electric potential is tapped at the guide wire 24 and transmitted to the ECG display 10 via the connecting cable 26. The two legs 47 48 are part of the plastic material clamp 45 having two gripping legs 49, 50 connected to the legs 47, 48 through a film hinge 51. By pressing the gripping legs 49, 50 together, the legs 47, 48 are moved apart to embrace the guide wire 24. When the gripping legs are then released, the guide wire is clamped to the metal plate 46. The clamp 25a may be clamped at any position of the exposed section of the guide wire 24.

What is claimed is:

1. A connecting device for an intra-atrial ECG lead comprising a connecting cable, said connecting cable including a single wire conductor and an insulation coverings the connecting cable having a first end provided with a first connector for connection to an electric lead of a vena cava catheter and having a second end provided with a second connector; an adapter with a first input adapted to be connected to an ECG clamp, a second input adapted to be connected to the second connector of the connecting cable, an output adapted to be connected to a patient cable of a display; the second connector having a conductive sleeves said conductive sleeve including a first portion electrically connected to the second end of the single wire conductor of the connecting cable, the conductive sleeve including a terminal end socket portion adapted to fit a plug portion of the second input to form a single electrically conductive connection path between the conductive sleeve and the single wire conductor, and said conductive sleeve further including a conductive shaft portion adjacent said terminal end socket portion having a larger outer diameter than said terminal end socket portion, and said conductive shaft portion being adapted to be clamped by an ECG clamp.

2. The connecting device as defined in claim 1 including a patient cable connected to at least one ECG clamp, and one of said at least one ECG clamp being connected to the larger diameter conductive shaft portion of the second connector.

3. The connecting device as defined in claim 1, wherein the first connector of the connecting cable is a clamp adapted to be clamped onto a catheter guide wire from the side.

4. The connecting device as defined in claim 1 wherein the first connector of the connecting cable has an exterior insulated contact sleeve.

5. The connecting device as defined in claim 1 wherein the larger diameter conductive shaft portion and the terminal end socket portion are arranged coaxially in mutual projection from the first portion of the conductive sleeve.

6. The connecting device as defined in claim 1 wherein the terminal end socket portion is adapted to be slipped clampingly over a plug portion of an adapter.

7. The connecting device as defined in claim 1 wherein the second connector includes a grip portion, and the larger diameter conductive shaft portion and the terminal end socket portion are arranged coaxially in mutual projection from the grip portion of the second connector.

8. The connecting device as defined in claim 7 wherein the grip portion substantially encloses the first portion of the conductive sleeve.

* * * * *